United States Patent [19]

Czarnecki et al.

[11] Patent Number: 5,230,895
[45] Date of Patent: Jul. 27, 1993

[54] SUSTAINED RELEASED DELIVERY SYSTEM FOR USE IN THE PERIODONTAL POCKET

[75] Inventors: Ronald F. Czarnecki, Palm City, Fla.; David L. Williams, Reading, Mass.

[73] Assignee: Copley Pharmaceutical Inc., Canton, Mass.

[21] Appl. No.: 517,566

[22] Filed: May 1, 1990

[51] Int. Cl.$^5$ .......................... A61F 2/02; A61K 9/14; A61K 25/04; A61K 47/44
[52] U.S. Cl. .................................. 424/422; 424/424; 424/426; 424/434; 424/435; 424/443; 424/444; 424/456; 424/462; 424/484; 424/486; 433/229; 514/786; 514/944
[58] Field of Search ............... 424/422, 424, 426, 434, 424/435, 443, 444, 456, 462, 484, 486; 433/229; 514/944, 786

[56] References Cited

U.S. PATENT DOCUMENTS

| | | | |
|---|---|---|---|
| 4,180,320 | 10/1988 | Baker | 424/493 |
| 4,515,771 | 5/1985 | Fine | 424/52 |
| 4,569,837 | 2/1986 | Suzuki et al. | 424/78 |
| 4,764,377 | 8/1988 | Goodson | 424/435 |
| 4,919,939 | 4/1990 | Baker | 424/493 |
| 4,933,172 | 6/1990 | Clark, Jr. et al. | 424/49 |

FOREIGN PATENT DOCUMENTS

0429224A1  5/1991  European Pat. Off.

OTHER PUBLICATIONS

Eastman, "Sustained Release with Myverol 18-92 Distilled Monoglyceride", Publication No. 2FD-84, pp. 1-2, 1987.
Eastman Publication No. ZM-1H, May 1988, entitled "Food Emulsifiers".
Deasy et al., *J. Pharm. Pharmacol.* 1989, 41:694-699 (Feb. 27, 1989), pp. 694-699.
Larsen, T., *J. Periodontol* (Jan. 1990), pp. 30-34.
Engstrom et al., *Proceedings of the 15th International Symposium on Controlled Release of Bioactive Materials*, Basel Aug. 15-19, 1988, pp. 105-106.
Ericsson et al., Proceed. Intern. Sump. Control Rel. Bioact. Mater., 15 (1988), pp. 382-383.
Landh et al., *Emulsification of the Cubic Liquid Crystalline Phase in the Monoolein-Lecithin-Water System:*, Publication date unknown.
Engstrom, S., *Lipid Technology* vol. 2, No. 2 (Apr. 1990), pp. 42-45.
Larsen, K., *J. Phys. Chem.* vol. 93, No. 21, 1989, pp. 7304-7314.

*Primary Examiner*—Thurman K. Page
*Assistant Examiner*—Carlos Azpuru
*Attorney, Agent, or Firm*—Lahive & Cockfield

[57] ABSTRACT

An in vivo method is described for treating a subject for periodontal disease by placing a mixture of a glyceride composition and a therapeutic agent in the periodontal pocket of subject such that the therapeutic agent is released in a sustained manner. The glyceride composition is selected such that the mixture of the glyceride composition and the therapeutic agent is capable of forming a gel in the environment of the periodontal pocket. Also described is a sustained release delivery system comprising the mixture of the glyceride composition and therapeutic agent.

19 Claims, 4 Drawing Sheets

SUSTAINED RELEASED DELIVERY SYSTEM FOR USE IN THE PERIODONTAL POCKET

GOVERNMENT SUPPORT

The invention described herein was supported by a grant from the National Institutes of Health.

FIELD OF THE invention

This invention relates to methods and compositions for treating periodontal disease in a site-specific and sustained release manner.

BACKGROUND

Periodontal disease is a major cause of tooth loss in adults over thirty-five years of age. It is caused by bacteria found in plague which is a film that constantly forms on teeth. The bacteria produce toxins which irritate the gums eventually destroying the attachment of the gums to the teeth. Infections to the bone develop beneath the gums and the gingival sulcus deepens to form a periodontal pocket.

Periodontal disease can be treated successfully if detected at an early stage. At the early stage, often called gingivitis, only the gum tissue is affected and if the condition is not kept under control it can lead to a more advanced condition called periodontitis. Periodontitis can affect the gums, bone and the supporting structures surrounding the teeth.

Some presently available means for treating periodontal disease in a non specific manner include long acting capsules or tablets held in the mouth, buccal implants for releasing drugs into the saliva, topically applied gels, and topically applied drug containing bandages. Other means used to treat periodontal disease in a more site-specific manner include impregnated or drug releasing forms of dental floss and solid absorbable fibers of polyglycolic acid with therapeutic agents incorporated therein.

Superficial drug delivery to the periodontal pocket can be ineffective for several reasons. During periodontal disease, gum tissue within the pocket becomes inflamed and surrounds the necks of the teeth. The inflamed areas surrounding the teeth can prevent diffusion of the therapeutic agent to the infected area if the agent is applied superficially. Further, crevicular fluid (similar compositionally to plasma) continuously is produced by the lining of the periodontal pocket when a subject has a periodontal disease. The production of crevicular fluid causes an outward flow away from the lining of the pocket making it difficult to apply therapeutic agents to the periodontal pocket in a manner allowing diffusion of the agents through the crevicular fluid to the desired site.

An interpocket drug delivery device is described in U.S. Pat. No. 4,764,377 issued to Goodson on Aug. 16, 1988. Goodson describes the use of a polymeric matrix, such as ethylene vinyl acetate co-polymer, as a packing containing a therapeutic agent. The therapeutic agent diffuses out of the polymeric packing providing continuous therapy for the treatment site. The packing of Goodson is not placed in the periodontal pocket in a solution or paste form.

SUMMARY OF THE INVENTION

The present invention provides a method for site-specific delivery of a therapeutic agent to the periodontal pocket by a delivery system capable of conforming to a subject's periodontal pocket. The drug delivery system of this invention is advantageous because it can be placed in a subject's periodontal pocket in solution or paste form and is capable of gelling in the environment of the periodontal pocket providing intimate contact with the periodontal tissues of the subject. Periodontal pockets can vary in size from one subject to another and a delivery system which is shaped for intimate contact with the periodontal pocket of one subject may not function as well in another subject. The gel formed in this invention is specifically conformed to the shape of the subject's pocket allowing intimate contact with the periodontal tissue of a subject on an individual basis.

This invention further pertains to an in vivo method for treating a subject for periodontal disease by placing a mixture of a glyceride composition and a therapeutic agent in the periodontal pocket of the subject. The therapeutic agent is released in a sustained manner within the periodontal pocket. The mixture of the glyceride composition and the therapeutic agent is selected such that it is capable of forming a gel in the environment of the periodontal pocket.

The invention further pertains to a sustained release delivery system containing the mixture of the glyceride composition and the therapeutic agent and packaged delivery systems containing the mixture of the glyceride composition and the therapeutic agent in a container preferably provided with instructions for using the mixture to treat periodontal disease.

This invention further pertains to a method for forming a drug delivery system for site-specific delivery of a therapeutic agent to the periodontal pocket of a subject. The drug delivery system is formed by mixing an effective amount of a therapeutic agent with a glyceride composition to form a drug delivery system. The formed delivery system is capable of gelling in the environment of the periodontal pocket. The method can further have a step of placing the mixture in a container.

It is an object of this invention to provide a multiple phase drug delivery system which changes from a solution or paste phase to a gel when applied in vivo.

It is another object of the invention to provide a sustained release delivery system which is biodegradable.

It is yet another object of the invention to provide a method and delivery system for treatment of periodontal disease in a continually sustained manner.

It is yet another object of the invention to provide a method and means for treating periodontal disease.

DETAILED DESCRIPTION

Figure 1:
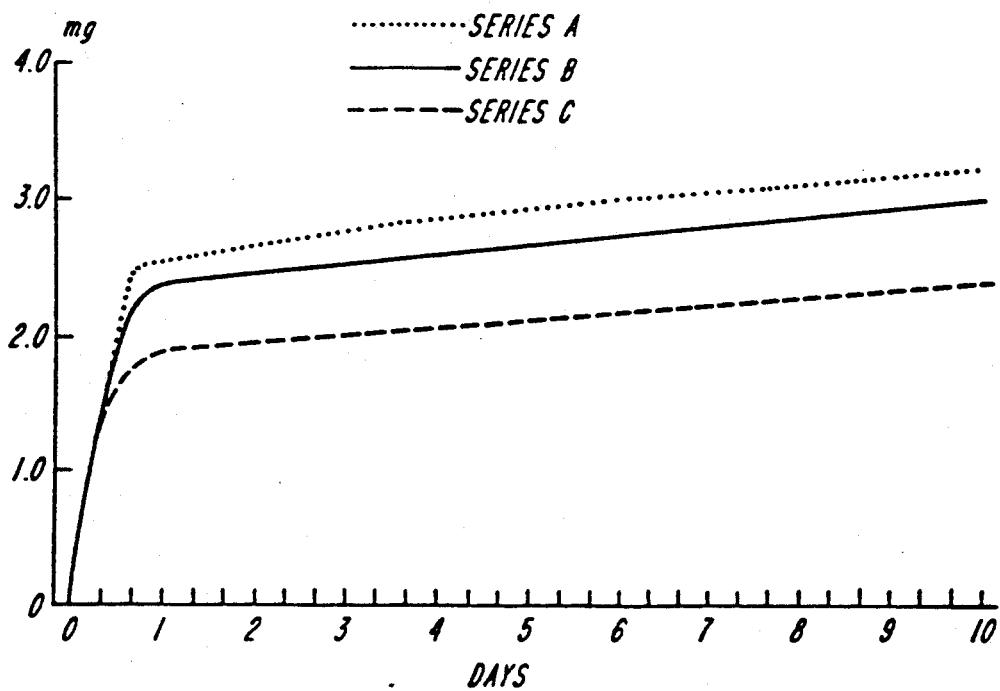
FIG. 1 is a graph depicting the release of tetracycline hydrochloride from a Myverol ® 18-92 gel over a ten day period.

The in vivo method of this invention is for treating a subject for periodontal disease. The method includes placing a mixture of a glyceride composition and a therapeutic agent in the periodontal pocket of the subject whereby the therapeutic agent is released in a sustained manner within the periodontal pocket. The mixture of the glyceride composition and the therapeutic agent forms a gel and conforms to the periodontal pocket of the subject in the environment of the periodontal pocket.

The term subject for purposes of this invention is intended to include living organisms susceptible to periodontal disease, e.g. mammals. Examples of subjects include humans, dogs, cats, horses, and cows.

The term periodontal disease for purposes of this invention is intended to include diseases which create a periodontal pocket in an individual. Periodontal diseases are typically caused by bacteria found in plague which produce toxins capable of irritating the gums. Examples of periodontal diseases include gingivitis and periodontitis.

The term mixture for purposes of this invention include mixtures having a viscosity capable of at least some flow properties. The mixture should have enough fluidity to flow into the pocket but yet be capable of gelling so it stays in the pocket. Examples of such mixture include liquids, pastes, or slurries.

The mixture can be placed into the periodontal pocket of the subject using conventional techniques. The mixture can be squeezed from a tube or it can be placed using a syringe having a non-penetration needle, for example. Any placement technique capable of inserting the mixture into the periodontal pocket would be suitable.

The term glyceride composition for purposes of this invention include compositions capable of forming a gel when containing the therapeutic agent and when contacted by the periodontal tissue or crevicular fluid. The gel is formed when the composition becomes hydrated and swells. The glyceride composition is substantially free of water. Substantially free of water includes glyceride compositions which contain a limited amount of water as long as the amount is sufficiently small to prevent complete gelling of the glyceride composition outside of the periodontal pocket.

The preferred glyceride composition of the present invention comprises at least 75 percent monoglycerides and has an iodine value of at least about 3, preferably at least about 10, most preferably at least about 20. The remaining 25 percent of glyceride composition can contain other ingredients as long as the ingredients do not significantly effect the gelling properties of the solution (i.e. the other ingredients cannot cause gelling outside of the periodontal pocket). Examples of other ingredients which may be added include diglycerides, triglycerides, glycerol, antioxidants, desiccants, or food preservatives.

The more preferred glyceride solution contains at least 90 percent monoglycerides and has an iodine value of at least 50, most preferably at least 90. Examples of most preferred glyceride compositions include Myverol ® 18-92 and Myverol ® 18-99, distilled monoglycerides, trademark products of Eastman Chemical Products, Incorporated, Kingsport, Tenn. For purposes of this invention, the term "Myverol composition" is intended to encompass compositions having the same or substantially the same constituents as the Myverol ® distilled monoglyceride compositions produced by Eastman Chemical Products, e.g., Myverol ® 18-92 and Myverol ® 18-99.

Myverol ® 18-92 is a distilled monoglyceride composition derived from sunflower oil containing a minimum of 90 percent monoglyceride. Myverol ® 18-92 is semiplastic at room temperature and has a specific gravity of 0.90 at 80° C., a melting point of about 41° C., a maximum percent glycerol of 1.2 percent, a maximum acid value of about 3, and a maximum iodine value from about 105–115. Myverol ® 18-92 is also bio-available (digested in the body).

Myverol ® 18-99 is a distilled monoglyceride composition derived from low euric rapeseed oil containing 90 percent monoglycerides. Myverol ® 18-99 is semiplastic at room temperature and has a specific gravity of 0.93 at 80° C., a melting point of about 35° C., a maximum percent glycerol of 1.2 percent, a maximum acid value of 3.0, and an iodine value from about 90 to about 95. Myverol ® 18-99 is also bioavailable.

The term therapeutic agent for purposes of this invention is intended to include substances capable of treating periodontal disease. It further is intended to include the free form, salt thereof, or a chemically modified form. A chemically modified form of a therapeutic agent is a form structurally similar and capable of achieving the same intended function. Examples of classes of therapeutic agents which can be used in this invention include anti-inflammatory agents and anti-microbial agents.

Anti-inflammatory agents are agents capable of reducing the inflammation of the gum tissue or supporting structures surrounding the teeth caused by periodontal disease. The anti-inflammatory agent can be steroidal or non-steroidal. Examples of non-steroidal anti-inflammatory agents include indomethacin, eugenol, flubiprofen and ibuprofen. An example of a steroidal agent is hydrocortisome.

Anti-microbial agents ale agents capable of suppressing the growth or activity of microorganisms allowing them to combat infections. Examples of classes of anti-microbial agents include antibiotics, iodine solutions, merourials, sulfonamides, nitroimidazoles, bisguanides or phenolics. Specific examples of agents within these classes include metronidazole and chlorhexidine.

Antibiotics are art-recognized and are chemical substances produced by microorganisms which suppress the growth of other microorganisms. However, herein the term is intended to include both naturally occurring and chemically synthesized antibiotics. Examples of antibiotics include tetracycline, minocycline, doxycycline, vanomycin, erythromycin, penicillin, bacitracin, kanamycin, and neomycin.

Other types of therapeutic agents which can be used in the present invention include immune suppressive or stimulatory agents such as methotrexate or leubamiasole, desensitizing agents such as stronium chloride or sodium fluoride, odormasking agents such as peppermint oil or chlorophyll, local anesthetic agents such as lidocaine or benzocaine, antioxidants such as alphatocopherol and butylated hydroxy toluene, or oxidizing complexing agents such as peroxides.

Another type of therapeutic agent which is useful in the present invention is an agent exhibiting anti-collagenase activity. These types of agents are particularly preferred because they are capable of interfering with enzymes capable of breaking down the tissues associated with various forms of periodontal disease. Tetracycline exhibits such activity.

An effective amount of the therapeutic agent is mixed with the glyceride composition. An effective amount of the therapeutic agent is that amount capable of eliminating or significantly reducing the symptoms associated with periodontal disease when released from the gel. An effective amount can be determined on an individual basis and will be based, at least in part, in consideration of the severity of symptoms to be treated (e.g., the amount of crevicular fluid being produced), the results sought, and the type of therapeutic agent used in the drug delivery system. Thus, an effective amount can be determined by one of ordinary skill in the art employing such factors using no more than routine experimentation. For treating an early stage periodontal disease with a mixture of Myverol ® and tetracycline, amounts in the range of about 5.0 to about 40 percent by weight are preferred.

The term periodontal pocket for purposes of this invention is the pocket created when the gingival sulcus deepens during periodontal disease. This term is art recognized and one of ordinary skill in the art would know what is meant by such language.

The term sustained manner for purposes of this invention is intended to encompass a manner which is prolonged for a selected period of time sufficient to achieve the desired therapeutic effect. This period varies depending upon at least such factors as the severity of symptoms and the therapeutic agent selected. Typical time periods for antibiotics, for example, would be up to ten days. Other therapeutic agents may be delivered to the periodontal pocket for shorter periods of time, such as, three to five days and some agents for longer periods of time up to several months.

The mixture of the glyceride composition and the therapeutic agent is capable of forming a gel in the environment of the periodontal pocket, e.g., when contacted by periodontal tissue or the the crevicular fluid. The gel is formed when the mixture becomes hydrated and swells. The crevicular fluid is the fluid emanating from the lining of the periodontal pocket during periodontal disease. The fluid is similar compositionally to plasma.

The mixture of glyceride composition and the therapeutic agent is capable of conforming to the periodontal pocket upon gelling. Conforming to the periodontal pocket is intended to include intimate contact with a substantial amount of the periodontal tissues of the periodontal pocket. Intimate contact is intended to include when the gel is contacting the surface of the periodontal tissue or is in close proximity to the periodontal tissues such that the therapeutic agent is allowed to diffuse from the gel into the crevicular fluid or periodontal tissue.

This invention further pertains to a sustained release delivery system comprising the mixture of the glyceride composition and the therapeutic agent. The delivery system of this invention preferably is biodegradable.

The biodegradable drug delivery system should be nontoxic to the subject and would not have to be removed from the periodontal pocket at the end of the treatment period.

This invention also pertains to packaged drug delivery systems containing the mixture of the glyceride composition and the therapeutic agent in a container. The delivery system is preferably packaged with instructions indicating how to use the delivery system for treating periodontal disease.

This invention further pertains to a method for forming a drug delivery system for site-specific delivery of a therapeutic agent to the periodontal pocket of a subject. The drug delivery system is formed by mixing an effective amount of a therapeutic agent with a glyceride composition to form a drug delivery system. The formed delivery system is capable of gelling in the environment of the periodontal pocket. The method can further have a step of placing the mixture in a container.

The preferred container is a tube, the most preferred container is the tubular portion of a syringe. The preferred packaged sustained release delivery system is a packaged syringe having a tubular portion containing the mixture of the glyceride composition and the therapeutic agent and a non-penetrating needle. This syringe can be removed from the package and the drug delivery system can be conveniently placed in the periodontal pocket of the subject by expelling the mixture from the syringe using a plunger. Preferably, the placement technique will be such that it can be done by lower skilled dental and medical personnel such as hygenists or other paramedical personnel.

The invention will be further illustrated by the following examples.

EXAMPLE 1

Drug Delivery System Containing Tetracycline Hydrochloride and Myverol ®18-92

A special cell (hereinafter flow-by cell) was designed and constructed to simulate the typical periodontal pocket. The flow-by cell has a lower rectangular section made of acrylic containing a milled trough ($3 \times 5 \times 1$ mm, width $\times$ length $\times$ depth) extending across a portion of its length. The cell also has a middle section made from a 2 mm thick rectangular silicon gasket of the same dimensions as the lower section. The gasket has a cut-out ($4 \times 25$ mm) which aligns with and extends further to each side of the milled trough forming a flow channel when the gasket is placed on top of the lower section. An acrylic top section containing inlet and outlet ports spaced 20 mm apart is placed on top of the gasket. The inlet and outlet ports are aligned with the cut out portions of the gasket which extend to the sides of the milled trough such that the fluid flows into one end of the flow channel and out of the other end.

The milled trough in the lower section of the flow-by cell was completely filled with a tetracycline hydrochloride/Myverol ® 18-92 semi-liquid paste at a tetracycline hydrochloride concentration of 30 percent by weight and the excess was removed by dragging a flat edge over the top of the trough. Approximately 13 mg of the paste was estimated to be present in the simulated pocket. After assembly of the flow-by cell, the pump tubing was connected to the inlet port, the cell was placed in a 37° C. oven, and the fluid flow was started.

Dulbecco's physiological phosphate buffered saline (hereinafter D-PBS, a product of Sigma Chemical Company, St. Louis, Mo.) was used as a solution for simulating the crevicular fluid (similar compositionally to plasma) and a peristaltic pump controlled the flow rate at 8 ml per day. Samples of the D-PBS were collected in a fraction collector over eight hour intervals for analysis. The D-PBS was made basic using sodium hydroxide and the concentration of the tetracycline was measured using a spectrophotometer at a wavelength of 380 nm. A standard curve was established at 380 nm using tetracycline hydrochloride as the standard and the art recognized methodology set forth in USPXXII p. 1343, the contents of which are hereby incorporated by reference. The concentration of tetracycline in the test solution was determined by measuring the absorbance and calculating the concentration from the standard curve.

Figure 2:
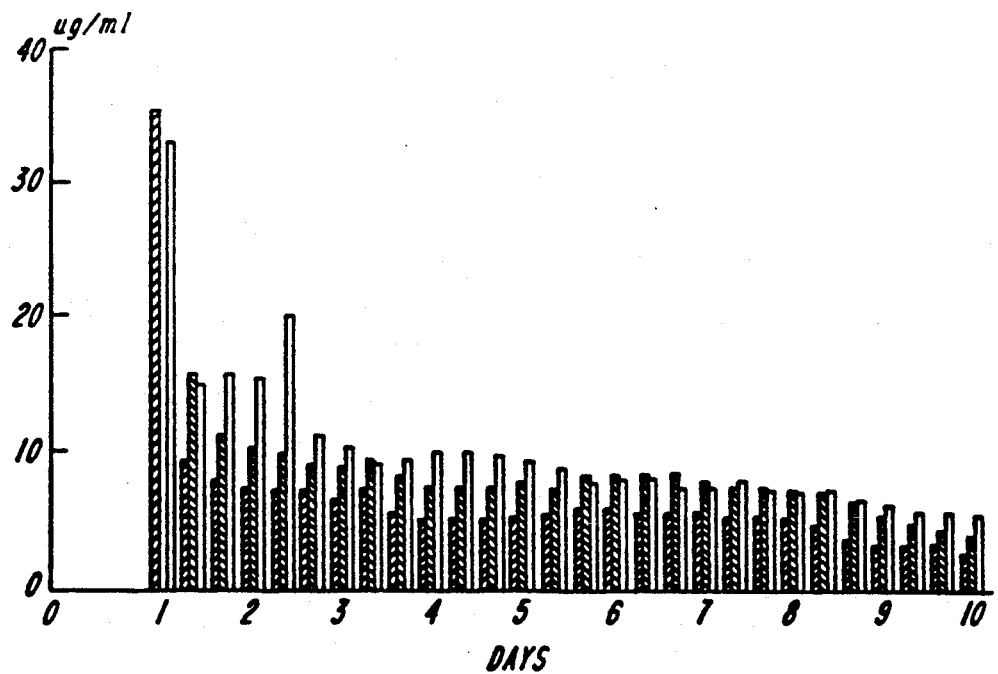
FIG. 2 is a bar graph depicting the concentration of tetracycline released from a Myverol ® 18-92 gel in a test solution representative of the crevicular fluid over a ten day period.

FIG. 1 shows the amount of tetracycline released from the Myverol ® 18-92 gel over a ten day period. A substantial amount of the tetracycline was rapidly released in the first 16 hours; however, there was a continued release of tetracycline which maintained the concentration in the test solution above a minimum inhibitory concentration (MIC) for ten days at the constant flow rate (FIG. 2). The MIC for tetracycline against important periodontal pathegans is estimated to be about 2 $\mu$g per ml.

EXAMPLE 2

Drug Delivery System Containing the Base Form of Tetracycline and Myverol ®18-92

Figure 3:
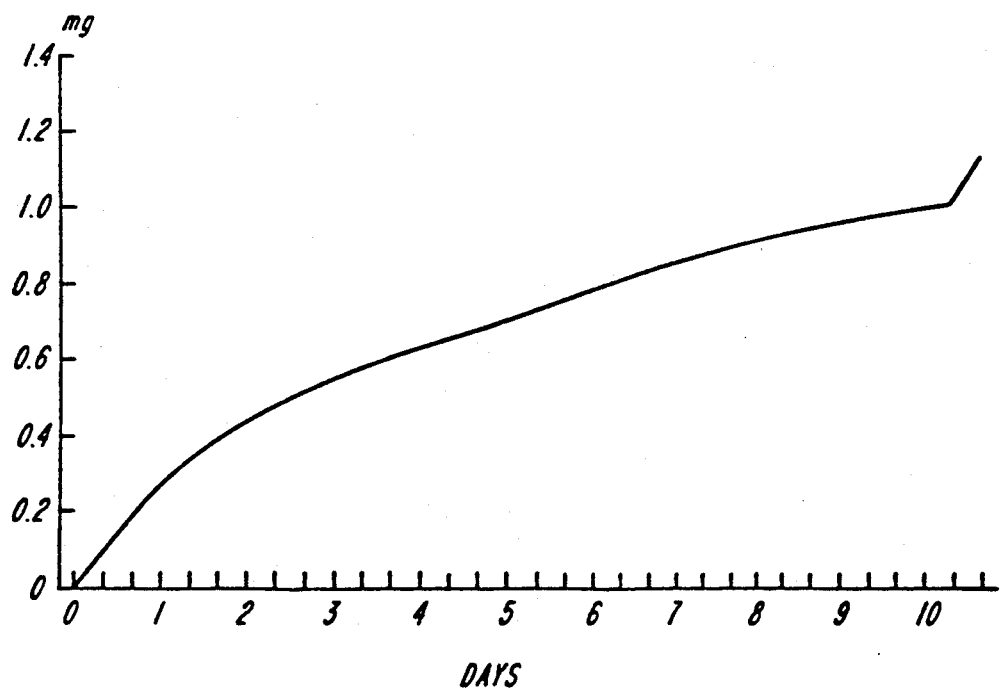
FIG. 3 is a graph depicting the release of a base form of tetracycline from a Myverol ® 18-92 gel over a ten day period.

Example 1 was repeated except a mixture of the base form tetracycline and Myverol ® 18-92 was used to form the gel in the flow-by cell. FIG. 3 shows the amount of tetracycline released from the gel into the test solution over a ten day period. The same technique as Example 1 was used to measure the concentration of tetracycline; however, the standard curve was established using the base form of tetracycline.

EXAMPLE 3

Drug Delivery System Containing a Preparation of Stearic Acid and the Base Form of Tetracycline and Myverol ®18-92

Figure 4:
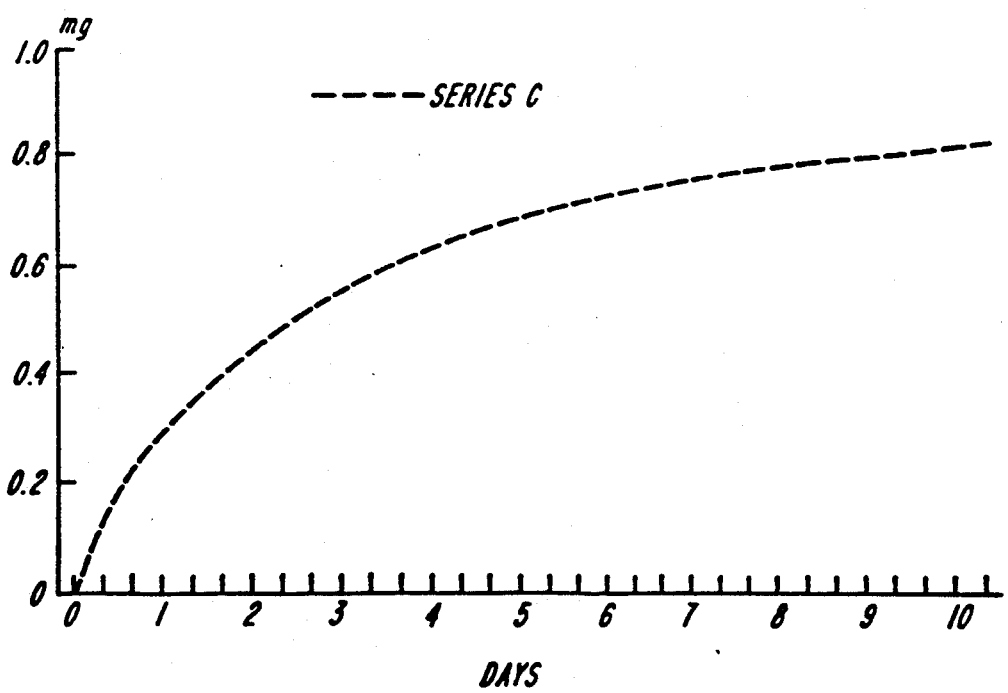
FIG. 4 is a graph depicting the release of the base form tetracycline from a Myverol ® 18-92 gel over a ten day period, the tetracycline having been added to the Myverol ® 18-92 as a preparation containing both stearic acid and tetracycline.
Figure 5:
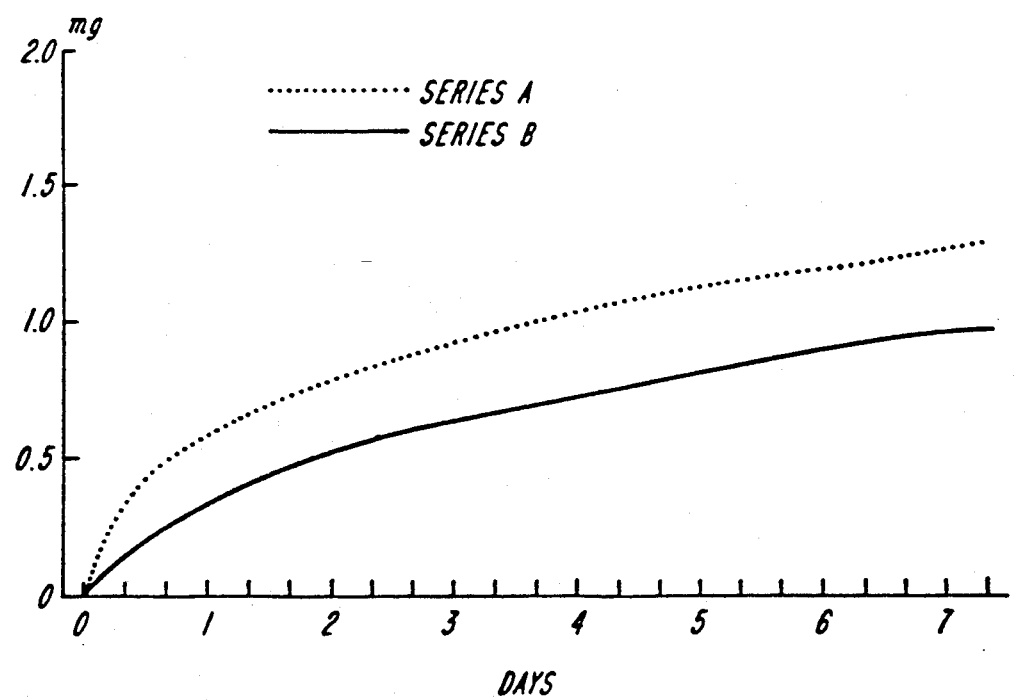
FIG. 5 is a graph depicting the release of oxytetracycline hydrochloride from a Myverol ® 18-92 gel over a seven day period.

Example 2 was repeated except a mixture containing the free base form of tetracycline (135 mg), stearic acid (94 mg) and Myverol ® 18-92 (600 mg) was used to form the gel in the flow-by cell. The free base form of tetracycline was mixed with the stearic acid using a dental amalgamator (WIG L-BUG made by Cresent Dental Manufacturing) and this was subsequently added to the Myverol ® 18-92. FIG. 4 shows the amount of tetracycline released from the gel into the test solution over a ten day period of time. The same technique as Example 1 was used to measure the concentration of tetracycline; however, the standard curve was established using the base form of tetracycline.

EXAMPLE 4

Drug Delivery System Containing the Base Form of Oxytetracycline and Myverol ®18-92

Example 1 was repeated except a mixture of the base form of oxytetracycline and Myverol ® 18-92 was used to form the gel in the flow-by cell. FIG. 8 shows the amount of oxytetracycline released from the gel over a ten day period. The same technique as Example 1 was used to measure the concentration of oxytetracycline; however, the standard curve was established using the base form of oxytetracycline and the absorbance was measured at a wavelength of 354 nanometers.

EXAMPLE 5

Drug Delivery System Containing Oxytetracycline Hydrochloride and Myverol ®18-92

Example 1 was repeated except a mixture of the hydrochloride form of oxytetracycline and Myverol ® 18-92 was used to form the gel in the flow by cell. FIG. 8 shows the release of oxytetracycline from the gel over a ten day period. The same technique as Example 1 was used to measure the concentration of oxytetracycline; however, the standard curve was established using oxytetracycline hydrochloride and the absorption was measured at a wavelength of 354 nanometers. Further, the D PBS fractions were not made basic prior to measuring the absorbance.

EXAMPLE 6

Drug Delivery System Containing Ibuprofen and Myverol ®18-92

Figure 6:
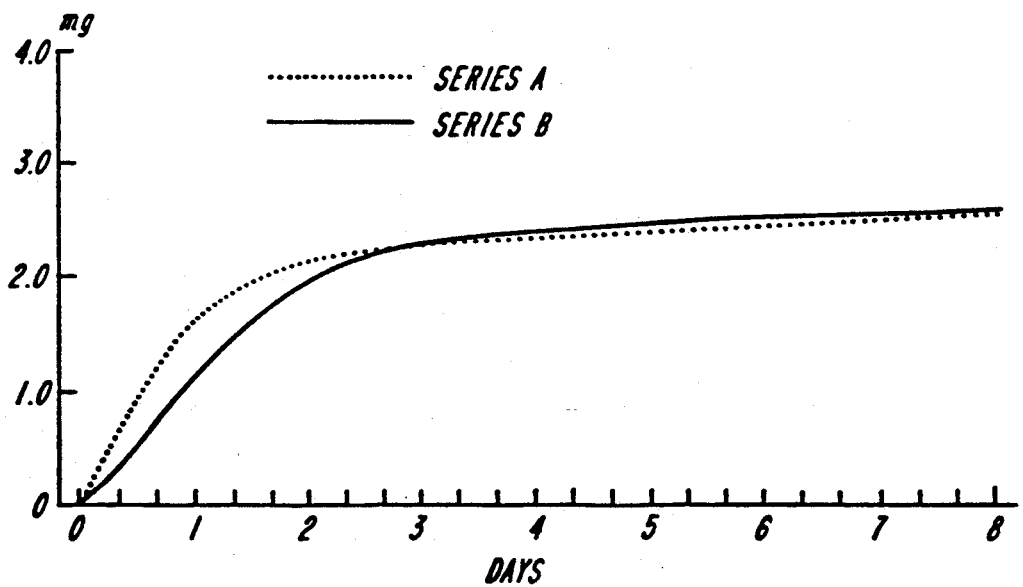
FIG. 6 is a graph depicting the release of ibuprofen and flubiprofen from a Myverol ® 18-92 gel over an eight day period.

Example 1 was repeated except a mixture of ibuprofen and Myverol ® 18-92 was used to form the gel in the flow-by cell. Series A of FIG. 6 shows the release of ibuprofen from the gel over an eight day period. The same technique as Example 1 was used to measure the concentration of ibuprofen; however, the standard curve was established using ibuprofen and the absorbence was measured at a wavelength of 222 nanometers. Further, the D-PBS fractions were not made basic prior to reading the absorbance.

EXAMPLE 7

Drug Delivery System Containing Flubiprofen and Myverol ®18-92

Example 1 was repeated except a mixture of flubiprofen and Myverol ® 18-92 was used to form the gel in the flow by cell. Series B of FIG. 6 shows the release of flubiprofen from the gel over an eight day period. The same technique as Example 1 was used to measure the concentration of flubiprofen; however, the standard curve was established using flubiprofen and the absorbence was read at a wavelength of 247 nanometers. The D-PBS fractions were not made basic prior to reading the absorbance.

EXAMPLE 8

Drug Delivery System Containing Metronidazole and Myverol ®18-92

Figure 7:
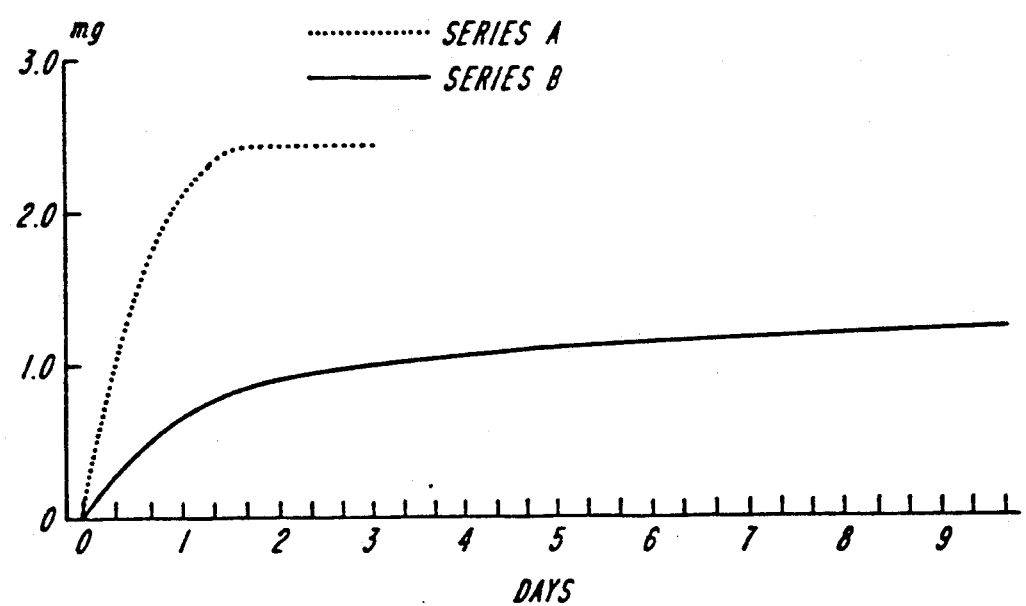
FIG. 7 is a graph depicting the release of metronidazole and chlorhexidine diacetate from a Myverol ® 18-92 gel over a nine day period.

Example 1 was repeated except a mixture of metronidazole Myverol ® 18-92 was used to form the gel in the flow-by cell. Series A of FIG. 7 shows the release of metronidazole from the gel over a nine day period. The same technique as Example 1 was used to measure the concentration of metronidazole; however, the standard curve was established using metronidazole and the absorbence was measured at a wavelength of 320 nanometers. The D PBS fractions were not made basic prior to measuring the absorbance.

EXAMPLE 9

Drug Delivery System Containing Chlorhexidine Diacetate and Myverol ®18-92

Example 1 was repeated except a mixture of chlorhexidine diacetate and Myverol ®18-92 was used to form the gel in the flow-by cell. Series B of FIG. 7 shows the release of chlorhexidine from the gel over a ten day period. The same technique as Example 1 was used to measure the concentration of chlorhexidine; however, the standard curve was established using chlorhexidine diacetate and the absorption was measured at a wavelength of 257 nanometers. The D-PBS fractions were not made basic prior to measuring the absorbance.

EXAMPLE 10

The Use of the Drug Delivery System Within the Periodontal Pocket

A 3 ml. mixture of tetracycline hydrochloride and Myverol® 18-92 at a concentration of 30 percent by weight tetracycline hydrochloride is placed in a syringe. The syringe is fitted with a 21 gauge non-penetrating needle. The mixture is gently expelled from the syringe into the bottom of the periodontal pocket of the patient. The needle of the syringe is withdrawn without pressing on the pocket. The excess of the mixture is wiped from the top of the pocket and the pocket subsequently sealed by covering the gingival crest and the base of the tooth (approximately 1 mm) with Iso-dent (a cyanoacrylate product of Ellman International Manufacturing, Inc., Hewlett, N.Y.), following the manufacturer's instructions for applying the Iso-dent with the applicator. The tetracycline hydrochloride and Myverol® 18-92 mixture is contacted with the periodontal tissue or crevicular fluid causing the mixture to gel and release tetracycline in a sustained manner into the crevicular fluid. After approximately one week, the sealant is optionally removed from the patient and the remaining mixture can optionally be washed out with a water syringe.

EQUIVALENTS

Those skilled in the art will be able to ascertain, using no more than routine experimentation, many equivalents of the specific embodiments of the invention described herein.

These and all other equivalents are intended to be encompassed by the following claims.

We claim:

1. An in vivo method for treating a subject for periodontal disease comprising, placing a mixture of a glyceride composition and a therapeutic agent in the periodontal pocket of the subject such that the therapeutic agent is released in a sustained manner within the periodontal pocket, wherein the mixture of the glyceride composition and the therapeutic agent is capable of forming a gel in the environment of the periodontal pocket and conforming to the periodontal pocket of the subject.

2. A method as claimed in claim 1 wherein the glyceride composition comprises at least 75 percent monoglycerides having an iodine value of at least 20.

3. A method as claimed in claim 1 wherein the glyceride composition comprises at least 90 percent monoglycerides having an iodine value of at least 50.

4. A method as claimed in claim 1 wherein the glyceride composition contains monoglycerides have a iodine value of at least 90.

5. A method as claimed in claim 1 wherein the glyceride composition is a Myverol composition.

6. A method as claimed in claims 1 or 3 wherein the therapeutic agent is an agent selected from the group consisting of anti-inflammatory, anti-microbial, immune-suppressive, immune-stimulatory, desensitizing, odor-masking, local anesthetic, anti oxidant, oxidizing, and appropriate combinations thereof.

7. A method as claimed in claims 1 or 3 wherein the therapeutic agent is an anti-inflammatory agent.

8. A method as claimed in claim 7 wherein the anti-inflammatory agent is non steroidal.

9. A method as claimed in claim 8 wherein the anti-inflammatory agent is selected from a group consisting of flubiprofen and ibuprofen.

10. A method as claimed in claim 7 wherein the anti-inflammatory agent is steroidal.

11. A method as claimed in claim 6 wherein the therapeutic agent is an anti-microbial agent.

12. A method as claimed in claim 11 wherein the anti-microbial agent is selected from the group consisting of antibiotics, iodine solutions, mercurials, nitroimidazoles, sulfonamides, bisguanides and phenolics.

13. A method as claimed in claim 12 wherein the anti-microbial agent is an antibiotic.

14. A method as claimed in claim 13 wherein the antibiotic is selected from the group consisting of tetracycline, minocycline, doxycycline, vanomycin, erythromycin, penicillin, bacitracin, kanamycin, and neomycin.

15. A method as claimed in claim 13 wherein the antibiotic is selected from the group consisting of tetracycline, oxytetracycline, minocycline, and doxycycline.

16. A method as claimed in claim 15 wherein the antibiotic is tetracycline.

17. A method as claimed in claim 6 wherein the anti-infective agent is selected from the group consisting of metronidazole and chlorhexidine.

18. A method as claimed in claims 1 or 3 wherein the therapeutic agent has anti-collagenase activity.

19. A method as claimed in claims 1 or 3 wherein about 5 to about 40 percent by weight of therapeutic agent is mixed with the glyceride composition.

* * * * *